United States Patent [19]

de Witt et al.

[11] 4,335,256

[45] Jun. 15, 1982

[54] PROCESS FOR MANUFACTURING D,l-β-BENZOYLMINO-ISOBUTYRIC ACID

[75] Inventors: Paolo de Witt; Enrico Diamanti, both of Rome, Italy

[73] Assignee: Sigma-Tau Industrie Farmaceutiche Riunite S.p.A., Rome, Italy

[21] Appl. No.: 961,102

[22] Filed: Nov. 16, 1978

[30] Foreign Application Priority Data

Nov. 30, 1977 [IT] Italy .................. 52004 A/77

[51] Int. Cl.³ ............................. C07C 101/12
[52] U.S. Cl. ..................... 562/450; 260/465 D
[58] Field of Search ..................... 562/443, 450

[56] References Cited

U.S. PATENT DOCUMENTS

| | | | |
|---|---|---|---|
| 2,461,842 | 2/1949 | Olin | 562/443 |
| 2,510,784 | 6/1950 | Lucas | 562/443 |
| 2,849,477 | 8/1958 | Dornow et al. | 562/450 |
| 3,489,793 | 1/1970 | Bertelli | 562/450 |

*Primary Examiner*—Natalie Trousof
*Assistant Examiner*—Vera C. Clarke
*Attorney, Agent, or Firm*—Robert E. Burns; Emmanuel J. Lobato; Bruce L. Adams

[57] ABSTRACT

A two-step process for manufacturing d,l-β-benzoylamino-isobutyric acid is disclosed, wherein in the first step benzamide is reacted with methacrylonitrile in the presence of an alkaline catalyst in an anhydrous solvent medium at atmospheric pressure, thus obtaining d,l-β-benzoylamino-isobutyronitrile, which, in the second process step, without necessarily being previously crystallized is directly hydrolyzed to d,l-β-benzoylamino-isobutyric acid.

7 Claims, No Drawings

PROCESS FOR MANUFACTURING d,l-β-BENZOYLAMINO-ISOBUTYRIC ACID

BACKGROUND OF THE INVENTION

1. Field Of The Invention

This invention relates to a process for manufacturing d,l-β-benzoylamino-isobutyric acid.

As known, d,l-β-benzoylamino-isobutyric acid is a valuable intermediate in the preparation of pharmaceuticals, e.g. triamcinolone acetonide esters which exhibit in topical use an effective antiphlogistic action. More particularly, this invention relates to a process for manufacturing d,l-β-benzoylamino-isobutyric acid whereby industrial application is facilitated since the starting materials employed during synthesis are widely used, readily available and quite inexpensive materials, and the reaction is carried out completely at atmospheric pressure. Moreover, by applying the process of this invention, a high purity product at a low cost with excellent yields is obtained.

2. Description Of The Prior Art

As disclosed in the prior art, the preparation of d,l-β-benzoylamino-isobutyric acid entails a cumbersome, multistep, low-yield process resulting in an expensive product which still requires complex purification procedures before being suitable for industrial application or further processing.

Floyd P. Kupiecki and Minor J. Coon in Biochemical Preparations, 1, 20 (1969) disclose the synthesis of β-aminoisobutyric acid, an indispensable intermediate in the prior art preparation of d,l-β-benzoylamino-isobutyric acid. In accordance with this disclosure, α-bromopropionic acid is reacted at 45°–50° C. with potassium cyanide to obtain α-cyanopropionic acid in a yield of only 52% based on α-bromopropionic acid which, before being subjected to further processing, has to be carefully separated from the unreacted bromoacid by distillation under reduced pressure. The α-cyanopropionic acid is then hydrogenated under pressure in the presence of platinum oxide; the hydrogenation requires about 6 hours. After removal of the spent catalyst by filtration and several subsequent steps of concentration, neutralization and filtration, a pasty residue is obtained which by a first crystallization and recrystallization from ethanol gives β-aminoisobutyric acid, in a yield of only 58%, based on α-cyanopropionic acid.

To obtain d,l-β-benzoylamino-isobutyric acid, the β-aminoisobutyric acid has finally to be reacted with a benzoyl halide, usually benzoyl chloride, under conventional reaction conditions.

SUMMARY OF THE INVENTION

An object of the invention is the preparation of d,l-β-benzoylamino-isobutyric acid by an economical procedure using readily available starting materials.

Another object of the invention is the preparation of d,l-β-benzoylamino-isobutyric acid by a procedure which avoids the difficult and dangerous steps required in prior processes and which provides a high yield of product.

A particular object of the invention is the preparation of d,l-β-benzoylamino-isobutyric acid by a process which avoids the use of high pressure.

A still further object of the invention is the preparation of d,l-β-benzoylamino-isobutyric acid by a process which does not require an expensive complicated procedure to isolate the desired product.

These and other objects are accomplished by means of the present invention whereby the synthesis of d,l-β-benzoylamino-isobutyric acid is accomplished in two steps.

According to the invention, d,l-β-benzoylamino-isobutyric acid, having the formula (1):

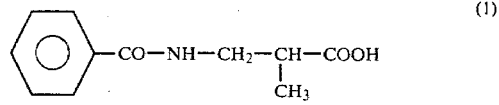

is prepared by the process which comprises:

(a) reacting benzamide with methacrylonitrile in the presence of an alkaline catalyst in an anhydrous solvent medium, at a temperature between about 80° and 100° C., thus obtaining d,l-β-benzoylamino-isobutyronitrile, having the formula (II):

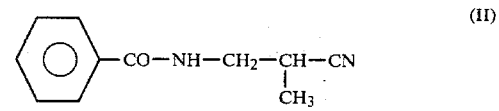

(b) hydrolyzing said d,l-β-benzoylamino-isobutyronitrile (II) to d,l-β-benzoylamino-isobutyric acid (1) in an alkaline medium in the presence of a lower alkanol having from 1 to 4 carbon atoms at a temperature between about 40° and 60° C.

DESCRIPTION OF THE INVENTION

Both steps of the process of the invention are carried out at atmospheric pressure.

In the first step, benzamide is reacted directly with methacrylonitrile in the presence of an alkaline catalyst in an anhydrous solvent medium, at the reflux temperature of the mixture, i.e. about 80°–100° C. and at atmospheric pressure, thus obtaining d,l-β-benzoylamino-isobutyronitrile. The reaction is generally considered to be complete after about 3–5 hours of refluxing. It is advisable to carry out the first step reaction away from the light, thereby avoiding the formation of polymerization products.

In the second step, the d,l-β-benzoylamino-isobutyronitrile obtained in the first step is directly subjected to hydrolysis in in an alkaline medium, in the presence of a lower alkanol having 1–4 carbon atoms, while heating the reaction mixture at the reflux temperature of the mixture, i.e. about 40°–60°. It is preferable to wash the d,l-β-benzoylamino-isobutyronitrile obtained by reaction of benzamide and methacrylonitrile with a solvent to remove waxy impurities prior to carrying out the hydrolysis; methyl t-butyl ether is a particularly suitable solvent for carrying out this simple washing step. It is not necessary to subject the nitrile product of the first step of the process to repeated crystallizations prior to the hydrolysis.

Hydrolysis of the d,l-β-benzoylamino-isobutyronitrile is regarded as being complete when ammonia ceases to develop. Upon acidification, a precipitate separates out of the reaction mixture. The precipitate complies perfectly with the analytical specifications of d,l-β-benzoylamino-isobutyric acid. It is apparent, therefore, that the foregoing operating conditions prevent the hydrolysis of the amide bond.

Non-limiting examples of suitable alkaline catalysts to be used in the process of the present invention are benzyltrimethylammonium hydroxide (TRITON B®), benzyltriethylammonium hydroxide, tetrabutylammonium hydroxide and mixtures thereof, benzyltrimethylammonium hydroxide being preferred.

Non-limiting examples of suitable anhydrous solvents to be used as reaction media in the process of the present invention are dioxane, tetrahydrofuran, dimethylsulfoxide and mixtures thereof, dioxane being preferred.

A mildly alkaline medium containing an alkaline reagent in a concentration of 0.5–2 N, more preferably 1 N, is employed for carrying out the second step hydrolysis; the alkaline reagent is preferably selected among $Na_2CO_3$, $K_2CO_3$, NaOH, KOH, i.e. alkali metal hydroxides and carbonates and similar alkaline compositions or mixtures thereof.

Among the lower alkanols having from 1 to 4 carbon atoms used in the hydrolysis step, methanol is preferred.

DESCRIPTION OF A PREFERRED EMBODIMENT

The following example further illustrates the best mode currently contemplated for carrying out the invention, but is not, however, intended to limit the scope of this invention.

Example

Step (a): Preparation of d,l-β-benzoylamino-isobutyronitrile 60.5 g. (0.5 moles) of benzamide were dissolved in 500 ml. of anhydrous dioxane in an approx. 2000-ml. reaction vessel equipped with a reflux condenser and the mixture was heated up to reflux temperature. Then, under vigorous stirring, 160 ml. (1.9 moles) of methacrylonitrile ($d^{20}0.80$) and 20 ml. of TRITON B (40%) solution in methanol were slowly added. The mixture was refluxed under constant stirring for approximately 3 hours. The behavior of the reaction was checked by thin-layer silica gel chromatography using $CHCl_3$:MeOH 97:3 as the eluant. When all the benzamide had reacted, the reaction mixture was dried in vacuo.

An amorphous mass was thus obtained which could easily be purified by a series of washings with methyl tert-butyl ether. These simple washings with methyl tert-butyl ether permitted a fairly crystalline product (89 g., 95% yield based on benzamide) to be obtained. This product upon elementary analysis, IR spectrum, and melting-point (determined on a mixture of a product sample with a sample of the authentic compound) was shown to be beyond doubt, d,l-β-benzoylamino-isobutyronitrile.

Step (b): Hydrolysis to d,l-β-benzoylamino-isobutyric acid 37.6 g. (0.2 moles) of d,l-β-benzoylamino-isobutyronitrile simply washed with methyl tert-butyl ether as shown in previous step (a) were dissolved in 200 ml. of methanol and then added to 190 ml. a 1 N NaOH solution and 38 ml. of 1 N $Na_2CO_3$.

The mixture was refluxed under vigorous stirring, until the development of ammonia was no longer noticeable (approx. 48–60 hrs.)

After methanol removal in vacuo, 3.7 g. of animal charcoal were added, the solution was then filtered and the resulting solution was strongly acidified with 6 N HCl. A precipitate was formed upon acidification.

The precipitate was collected, washed with water and then dried at 56° C. in an oven in vacuo. 33.20 g. of crystalline product (80% yield based on d,l-β-benzoylamino-isobutyronitrile) were obtained which upon elementary analysis, IR spectrum and melting point (determined on a mixture of a product sample with a sample of the authentic compound) was shown to be beyond doubt d,l-β-benzoylamino-isobutyric acid.

The advantages achieved by the process of this invention over the prior art process will be readily apparent to those skilled in this art.

These advantages can be summarized as follows:

(1) Both the cyanide treatment and the hydrogenation, which are troublesome and dangerous steps in any industrial process, are totally avoided.

(2) The use of superatmospheric pressure (in the hydrogenation step) is no longer necessary, the whole process being carried out at atmospheric pressure.

(3) As starting materials in the process of this invention, widely used and readily available products (benzamide and methacrylonitrile) are employed, which are notably cheaper than potassium cyanide and α-bromopropionic acid, the starting materials in the prior art process.

(4) By the process of the present invention, higher yields are obtained, whilst the intermediate product (d,l-β-benzoylamino-isobyronitrile) does not require isolation or crystallization. Conversely, the α-cyanopropionic acid, the key-intermediate in the prior art process, must be carefully separated from unreacted α-bromopropionic acid and potassium cyanide before being subjected to the hydrogenation step.

What is claimed is:

1. In a process for preparing d,l-β-benzoylamino-isobutyric acid, having the formula

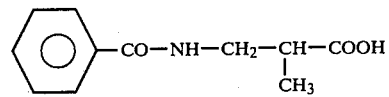

which comprises:

(a) reacting benzamide with methacrylonitrile in the presence of an alkaline catalyst in an anhydrous solvent medium, at a temperature of about 80° to 100° C., thus obtaining d,l-β-benzoylamino-isobutyronitrile, having the formula:

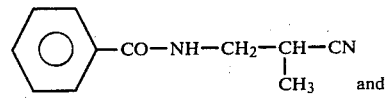

and (b) hydrolyzing said d,l-β-benzoylamino-isobutyronitrile to d,l-β-benzoylamino-isobutyric acid in an alkaline medium in the presence of a lower alkanol having from 1 to 4 carbon atoms at a temperature of about 40° to 60° C., the improvement wherein the reaction of said benzamide with methacrylonitrile is carried out in the presence of an alkaline catalyst which is a quaternary ammonium base selected from the group consisting of benzyl-trimethylammonium hydroxide, benzyl-triethylammonium hydroxide, tetrabutylammonium hydroxide and mixtures thereof.

2. The process of claim 1, wherein said anhydrous solvent medium is selected from the group consisting of dioxane, tetrahydrofuran, dimethylsulfoxide and mixtures thereof.

3. The process of claim 1, wherein said alkaline medium is selected from a solution of an alkaline reagent of the group consisting of $Na_2CO_3$, $K_2CO_3$, NaOH, KOH and mixtures thereof.

4. The process of claim 1 wherein said alkaline medium is a solution of an alkali metal hydroxide or carbonate in a concentration of about 0.5–2 N.

5. The process of claim 1, wherein said lower alkanol having 1–4 carbon atoms is methanol.

6. The process of claim 1, wherein step (a) is carried out substantially in the absence of light.

7. The process of claim 1, which comprises, before hydrolysis, subjecting d,l-β-benzoylamino-isobutyronitrile of step (a) to washing with methyl t-butyl ether.

* * * * *